United States Patent [19]
Doi

[11] Patent Number: 5,312,591
[45] Date of Patent: May 17, 1994

[54] COLOR TEST STRIP CARRYING PAD FOR CORRECTION

[75] Inventor: Kenichi Doi, Shiga, Japan

[73] Assignee: Kyoto Daiichi Kagaku Co., Ltd., Kyoto, Japan

[21] Appl. No.: 791,530

[22] Filed: Nov. 14, 1991

[30] Foreign Application Priority Data

Nov. 14, 1990 [JP] Japan ................................ 2-309128

[51] Int. Cl.⁵ ...................... G01N 31/22; G01N 33/50
[52] U.S. Cl. ........................................ 422/56; 422/57; 422/58
[58] Field of Search .................................. 422/56–58

[56] References Cited

U.S. PATENT DOCUMENTS

| | | | |
|---|---|---|---|
| 4,125,372 | 11/1978 | Kawai et al. | 422/56 X |
| 4,160,646 | 7/1979 | Furutani et al. | 422/56 X |
| 4,837,043 | 6/1989 | Engelmann et al. | 422/56 X |

*Primary Examiner*—Jill A. Johnston
*Attorney, Agent, or Firm*—Birch, Stewrt, Kolasch & Birch

[57] ABSTRACT

A color test strip for detecting predetermined substances which carries on a support at least one coloring pad and at least one pad for. The correction pad having a pH which is adjusted in relation to pH of the coloring pad. The color test strip can avoid false positive and false negative results.

4 Claims, 6 Drawing Sheets

COLOR TEST STRIP CARRYING PAD FOR CORRECTION

BACKGROUND OF THE INVENTION

1. Field of the Invention

The present invention relates to a color test strip carrying a pad for correction. More particularly, the present invention relates to an improvement of a color test strip for analyzing components contained in a liquid sample such as urine.

2. Description of the Related Art

Japanese Patent Kokai Publication No. 101491/1978 and corresponding U.S. Pat. No. 4,160,646 disclose a composite color test strip carrying a pad for correcting reflectance and various coloring pads and a method for analyzing various unusual materials contained in a sample by measuring the developed colors with various lights having different wavelengths to avoid influence of a colored sample. In the invention of this Japanese Patent Kokai Publication, the pad for correcting reflectance is made of a plain filter paper which is also used as a base material of the coloring pads and is not specially treated.

In general, when a material contained in a colored sample is measured with the coloring pad, different coloring substances have influences on tested items at different degrees, and a correction effect of the pad may be influenced by such coloring substances.

For example, when a concentration of nitrate in urine containing blood at a high concentration is measured, an untreated filter paper as a correction pad can avoid a false positive result, but sometimes a false negative result may be obtained.

SUMMARY OF THE INVENTION

An object of the present invention relates to a color test strip which can avoid both false positive and negative results.

According to the present invention, there is provided a color test strip carrying at least one coloring pad and at least one pad for correction pH of which is adjusted in relation to pH of the coloring pad.

The pH of the coloring pad is adjusted according to an item to be tested.

DESCRIPTION OF THE DRAWINGS

FIGS. 2 to 5 show the correction effects in the detection of protein.

DETAILED DESCRIPTION OF THE INVENTION

Figure 1A:
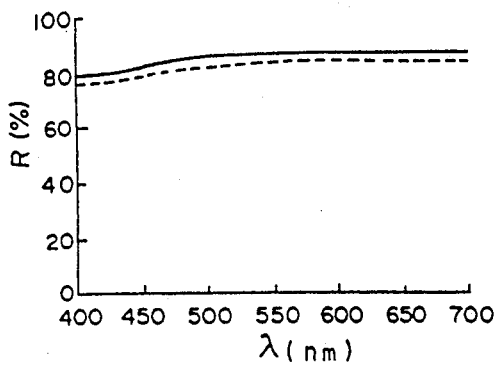
FIGS. 1A to 1H show the reflection spectra of the pad for correction of the present invention and the comparative pad for correction with various urine samples.
Figure 1E:
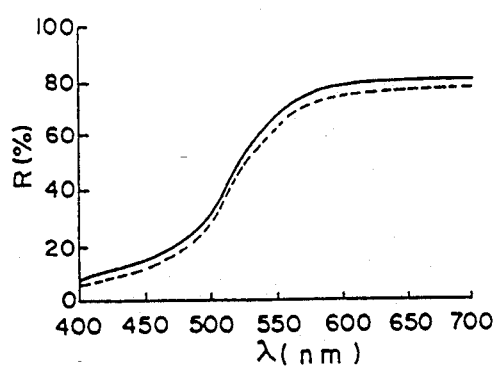
Figure 1B:
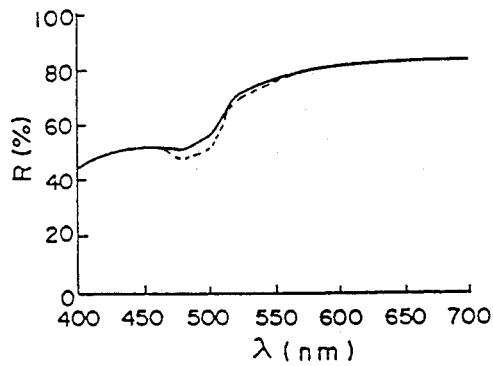

In the analysis of various components in urine as a liquid sample, the influence of the colored sample (urine) increases as the wavelength decreases. In general, the items to be measured in a short wavelength range include bilirubin, urobilinogen, nitrous acid and ketone bodies. Since, among them, bilirubin, urobilinogen and nitrous acid have narrow dynamic ranges, the pad for correction is required to have a high correction performance. In addition, a test paper which utilizes an azo coupling of bilirubin, urobilinogen and the like has a slightly lower specificity. For the purpose of accurate measurement, it is desirable to remove as many causes for error as possible.

When a behavior of coloring is examined with a test paper for each item using various actual samples, spectral characteristics of the coloring component varies with the test papers. It is found that such behavior substantially depends on pH of the test paper.

Hemoglobin is one of the coloring components in urine which cause spectral changes.

Since the test papers for bilirubin, urobilinogen and nitrous acid are strongly acidic, it is effective to use a strongly acidic pad for correction. In fact, when correction performances of a filter paper containing tartaric acid (I) and a filter paper containing no acid (II) are examined with various items, the filter paper (I) has much better correction performance than the paper (II) with bilirubin, urobilinogen and nitrous acid. In addition, an improvement is seen in a test strip for protein. The reason for such improvement may be that pH of the test strip for protein is about 3 and relatively strongly acidic.

Though the color test strip of the present invention may be a visual inspection type, it is preferably a color test strip with which a reflectance from the test strip is optically measured to detect the degree of developed color and the presence and a concentration of each component to be tested are detected.

The structure of the color test strip of the present invention may be the same as that of the color test strip disclosed in Japanese Patent Publication No. 12814/1981 and corresponding U.S. Pat. No. 4,125,372, though it is possible to modify it according to the purpose and use of the test strip.

pH of the pad for correction is easily adjusted by dipping a pad material (e.g. paper, woven or nonwoven fabric, etc.) in an aqueous solution of a colorless or substantially colorless acid or alkali. Examples of the acid are organic acids such as tartaric acid, citric acid, oxalic acid, phthalic acid, sulfosalicylic acid, metaphosphoric acid and the like; buffers which create an acidic condition; and acidic polymers. Examples of the alkali are buffers which create a alkaline condition such as sodium carbonate, sodium ethylenediaminetetraacetate, sodium tetraborate, trisodium phosphate and the like.

A concentration of the aqueous solution may be adjusted according to the intended pH of the pad for correction. When plural components are detected by providing plural coloring pads on the test paper, it is possible to make the correction for plural items with a single pad for correction having suitable pH though the optimum pH varies with the items to be detected. In fact, in below described Examples, the correction is made with a pad for correction having pH of 1.5 on the items for which the optimum pH is from 1 to 6.

After dipping the pad material in the above aqueous solution, it is pulled out from the solution and dried at room temperature or an elevated temperature to obtain the pad for correction.

Figure 6:
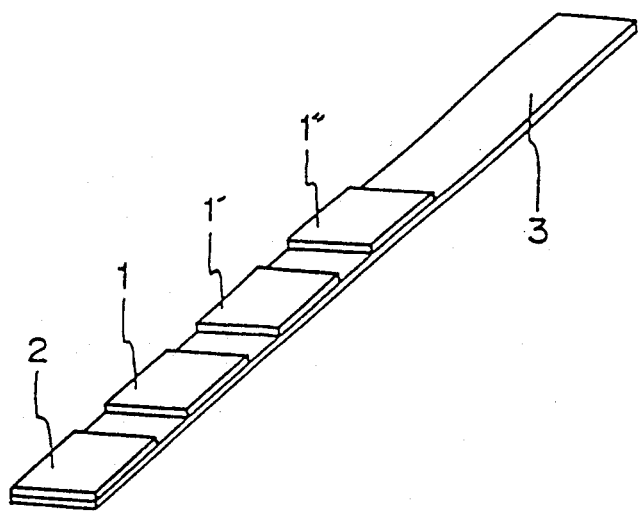
FIG. 6 is a perspective view of one example of the color test strip of the present invention.

The color test strip of the present invention carrying the pad for correction may have substantially the same structure as that disclosed in Japanese Patent Publication No. 12814/1981 and U.S. Pat. No. 4,125,372 the disclosure of which is hereby incorporated by reference, except that the pH of the pad for correction is suitably adjusted. Preferably, it has a structure of FIG. 6 which can detect plural items with one color test strip. The color test strip of FIG. 6 comprises, from one end of the test strip 3, a pad 2 for correction and coloring pads 1, 1', 1", - - - .

PREFERRED EMBODIMENTS OF THE INVENTION

The present invention will be illustrated by following Examples.

REFERENCE

FIGS. 1A to 1H show reflection spectra of the pads for correction when they were dipped in eight samples of urine.

FIG. 1A shows the reflection spectrum in case of light colored urine. From the comparison of other reflection spectra with FIG. 1A, it is understood that other spectra have various patterns.

Figure 1F:
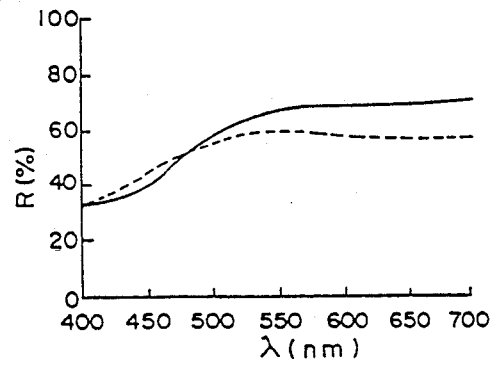
Figure 1C:
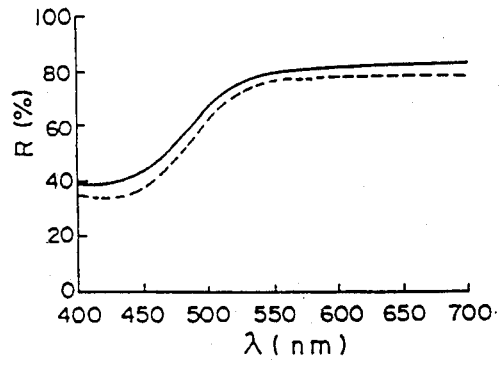
Figure 1G:
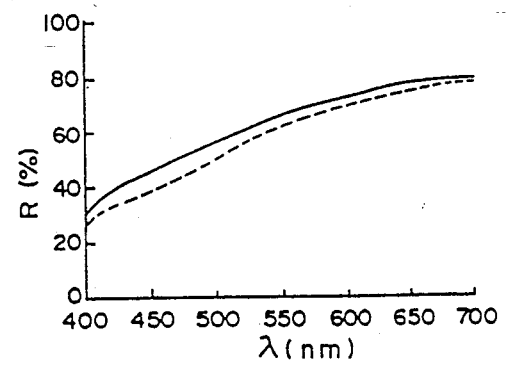
Figure 1D:
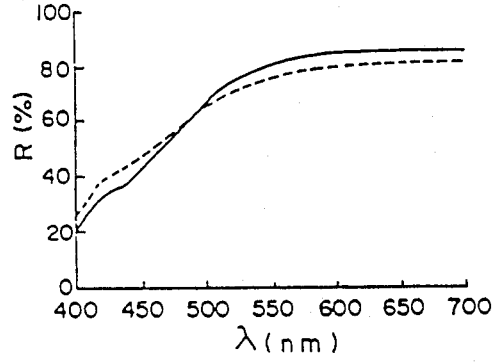
Figure 1H:
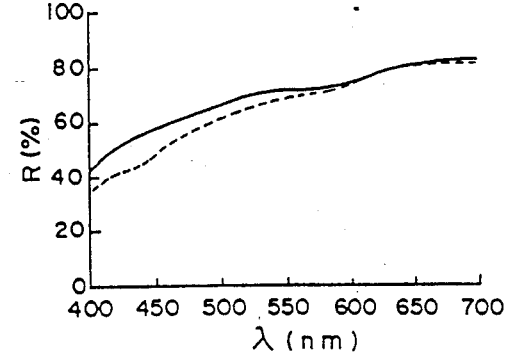

FIG. 1F shows the reflection spectrum in case of green colored urine, and has comparatively large absorption even in a longer wavelength range. In FIGS. 1A to 1H, the broken lines represent the reflection spectra of the pad for correction according to the present invention, while the solid lines represent those of a pad for correction which is described in Japanese Patent Kokai Publication No. 101491/1978 and corresponding U.S. Pat. No. 4,160,646 the disclosure of which is hereby incorporated by reference.

EXAMPLES

As samples, freeze stored colored urines (32 samples), freshly collected urines (3 samples) and pooled urines which were prepared as follows (5 samples) were used.

Whole blood was diluted with purified water to 2.5 times (hemolysis) and added to the pooled urine at a whole blood concentration of 0, 1, 2, 5 or 10 $\mu$l/ml.

The measurement was carried out using a color-difference meter (SZ-$\Sigma$ 80 manufactured by Nippon Denshoku Kogyo Co., Ltd.) at 37° C. with a sample amount of 8 $\mu$l. The number of measurement was one for the colored urine samples and five for the pooled urine samples.

As coloring pads, were used pads for protein, bilirubin, urobilinogen and nitrous acid, which were prepared by impregnating a filter paper (No. 514A manufactured by Toyo Filter Paper Co., Ltd.) with the same components as a commercially available urine test strip (Uriflet manufactured by Kyoto Daiichi Kagaku) except that a part of color developing agents are removed, and dried.

As a pad for correction, the same filter paper as above impregnated with tartaric acid (pH 1.5) was used.

For comparison, a filter paper containing no pH-adjusting agent was used as a pad for correction.

FIGS. 2 to 5 show the correction performances of the pad for correction with the items to be detected. The abscissa represents the sample numbers (40 samples) among which Nos. 36-40 were the pooled urine samples. The ordinate represents a concentration which is obtained by converting a calibration parameter (CP) according to the sensitivity curve. The calibration parameter is determined as follows:

With each of the coloring pads and the paper strip for correction, the reflection spectrum with water and that with the colored urine sample are measured at a specific wavelength. The reflection spectrum strength with water is Ra (from the coloring pad) or Ra' (from the pad for correction), and the reflection spectrum strength with the colored urine sample is Rb (from the coloring pad) or Rb' (from the pad for correction).

A coloring degree of the coloring pad CDt is expressed by log(1/Rb)−log(1/Ra), while a coloring degree of the pad for correction CDc is expressed by log(1/Rb')−log(1/Ra'). Then, CP is a difference between CDt and CDc (CDt−CDc). When CP is zero, a suitable correction is made. When CP is positive (CP>0), the correction is undercorrection so that the false positive result tends to be given. When CP is negative (CP<0), the correction is overcorrection so that the false negative result tends to be given.

Figure 2A:
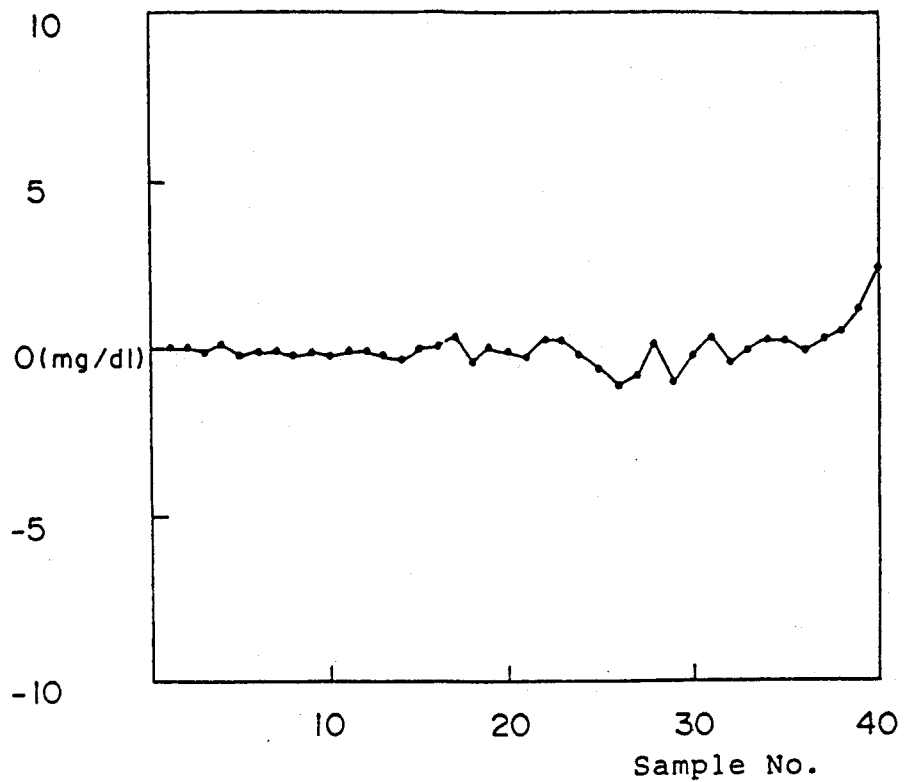
Figure 2B:
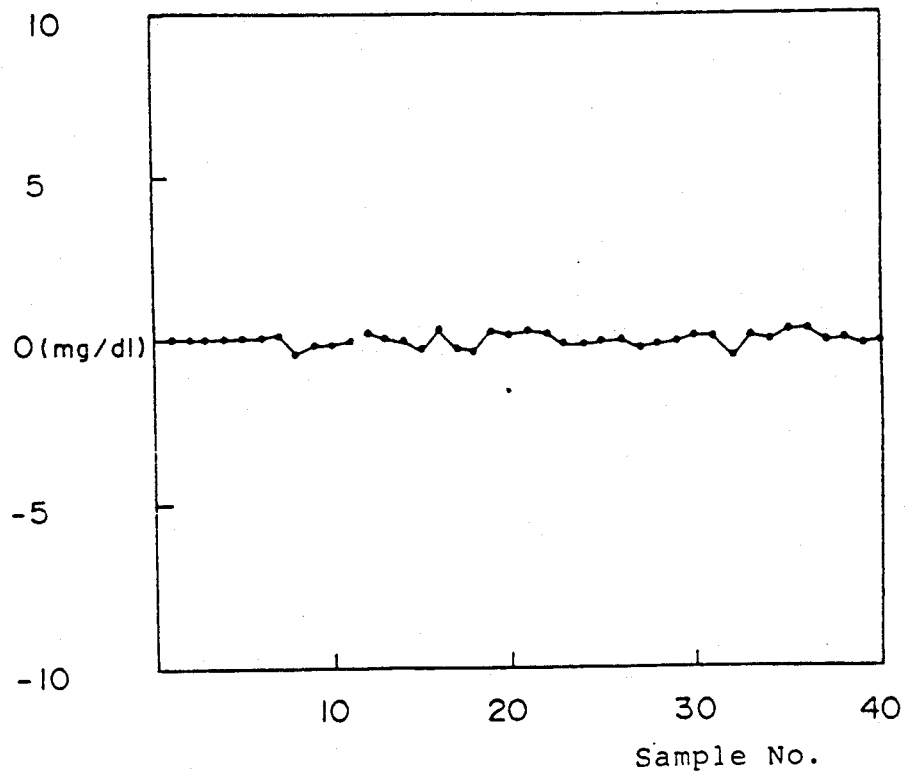

FIGS. 2A and 2B show the correction effects in the detection of protein. FIG. 2A shows the results when the comparative pad for correction was used, while FIG. 2B shows the results when the pad for correction of the present invention was used. Apparently, the pa for correction of the present invention provides better results. In particular, when the high concentration of the whole blood was added to the pooled urine sample, the correction can be made.

Figure 3A:
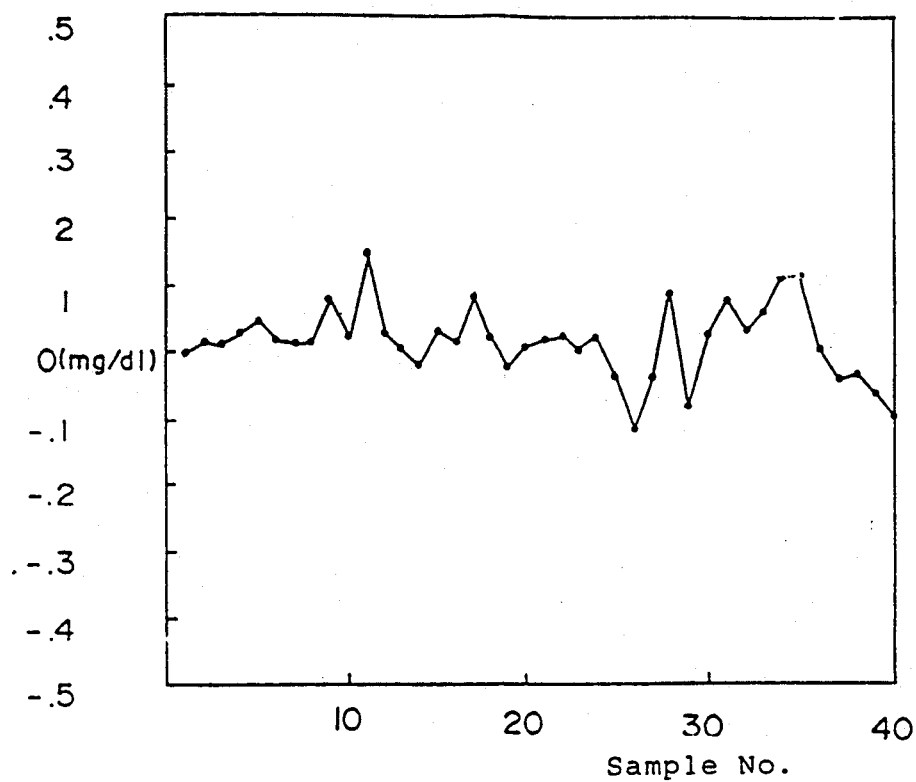
FIGS. 3A and 3B show the correction effects in the detection of bilirubin.
Figure 3B:
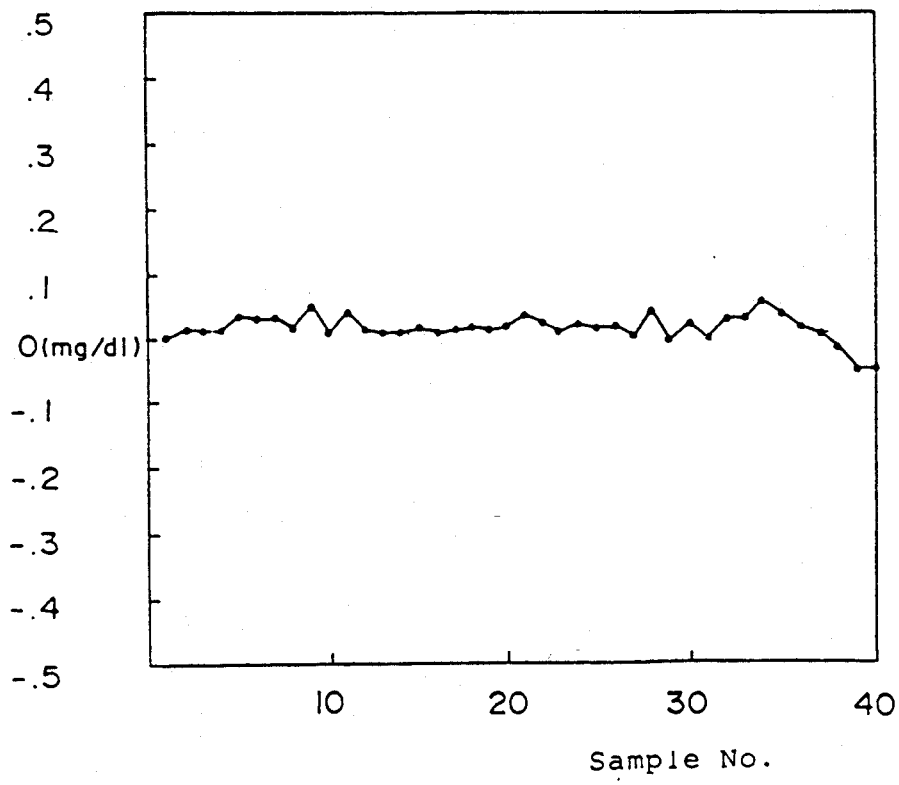
Figure 4A:
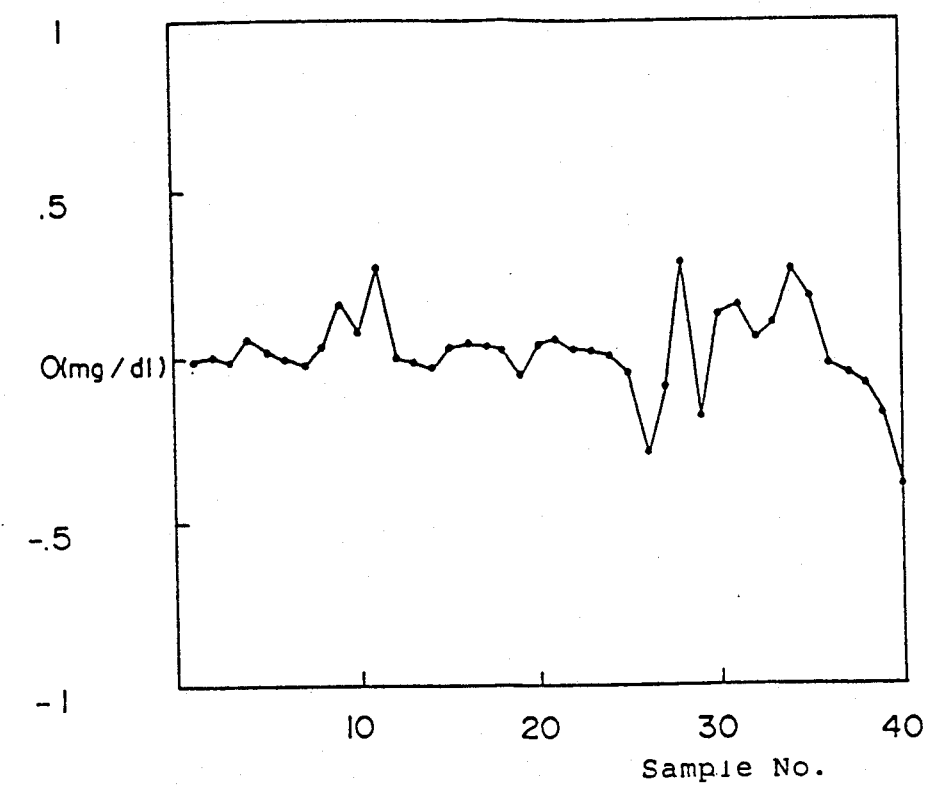
FIGS. 4A and 4B show the correction effects in the detection of urobilinogen.
Figure 4B:
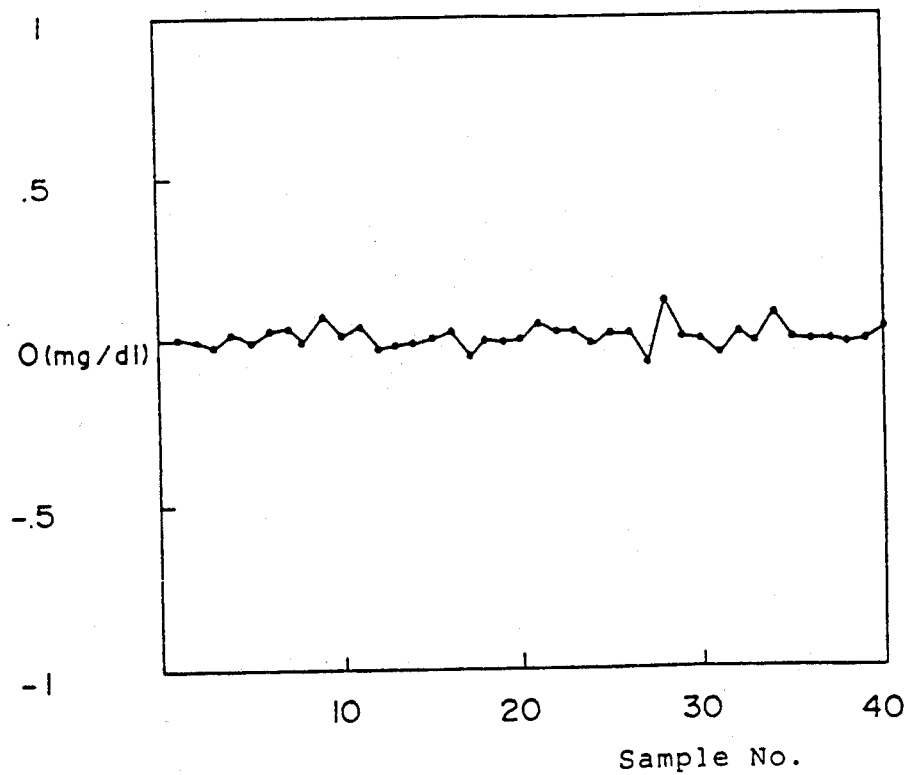
Figure 5A:
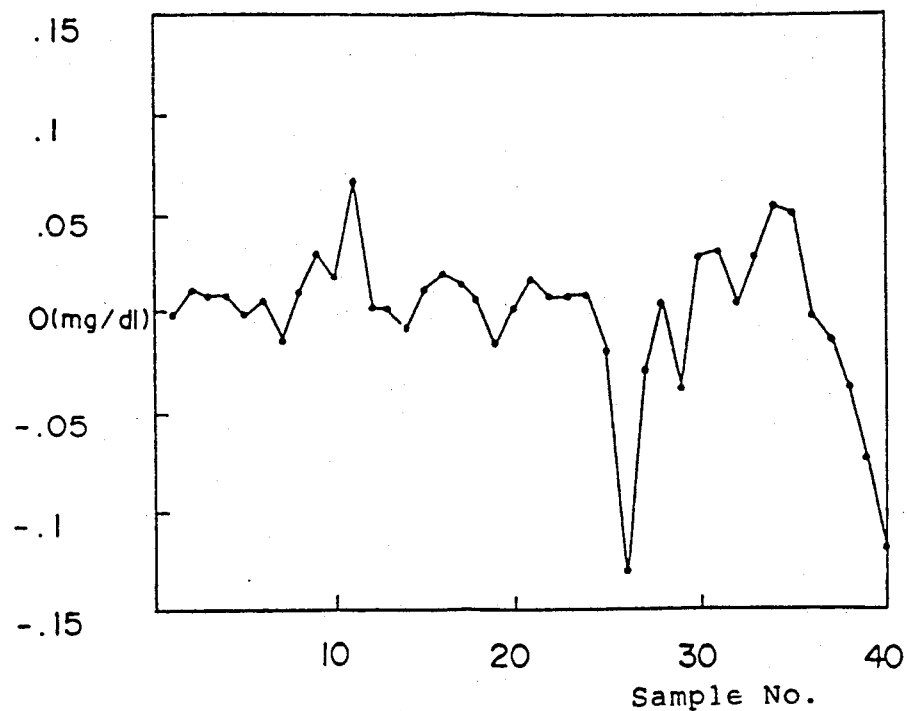
FIGS. 5A and 5B show the correction effects in the detection of nitrous acid.
Figure 5B:
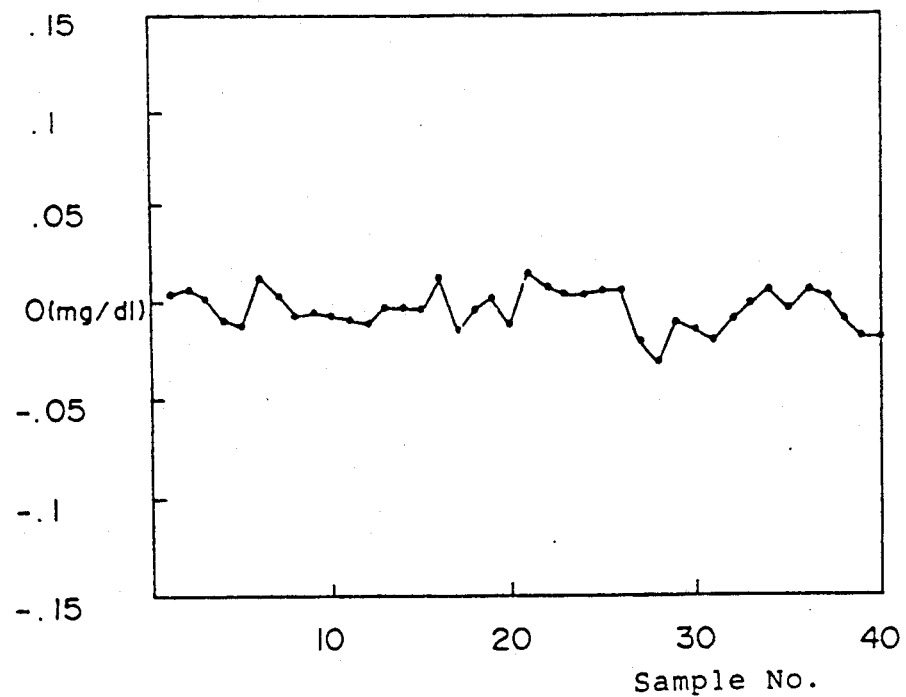

In the following figures, FIGS. 3A, 4A and 5A show the results when the comparative pad for correction was used, while FIGS. 3B, 4B and 5B show the results when the pad for correction of the present invention was used.

FIGS. 3A and 3B show the correction effects in the detection of bilirubin. The pad for correction of the present invention achieved substantially the same results as the comparative one.

FIGS. 4A and 4B show the correction effects in the detection of urobilinogen, and FIGS. 5A and 5B show the correction effects in the detection of nitrous acid. In both cases, the correction effects of the pad for correction of the present invention are much better than the comparative one.

Though the above explanation is made in case where the components are detected through the reflectance, the present invention can be applied to fluorometry or emission measurement.

What is claimed is:

1. In a color test strip for detecting the presence of at least one predetermined substance which comprises a support having disposed thereon at least one coloring pad which provides a color indication upon contact with a predetermined substance, and at least one pad for correction which does not provide a color indication upon contact with said predetermined substance, the improvement comprising:

said pad for correction being impregnated with an acid selected from the group consisting of tartaric acid, citric acid, oxalic acid, phthalic acid, sulfosalicylic acid, metaphosphoric acid and acidic polymers, and having a pH which is ±1.5 from the pH of said coloring pad.

2. The color test strip according to claim 1, wherein said pad for correction has impregnated therein a buffer which creates an alkaline condition.

3. The color test strip according to claim 1, wherein said coloring pad is capable of detecting a component selected from the group consisting of protein, bilirubin, urobilinogen and nitrous acid.

4. The color test strip according to claim 1, wherein said pad for correction has a pH of about 1.5.

* * * * *